United States Patent
Iwakuro et al.

(10) Patent No.: US 10,478,887 B2
(45) Date of Patent: Nov. 19, 2019

(54) DIE ABNORMALITY PREDICTION SYSTEM, PRESS MACHINE PROVIDED WITH THE SAME, AND DIE ABNORMALITY PREDICTION METHOD

(71) Applicants: Nidec-Shimpo Corporation, Nagaokakyo-shi, Kyoto (JP); Nidec Corporation, Minami-ku, Kyoto (JP)

(72) Inventors: Tetsuya Iwakuro, Nagaokakyo (JP); Takayuki Sawada, Nagaokakyo (JP); Masayuki Otani, Nagaokakyo (JP); Kazuyoshi Koga, Kyoto (JP); Takafumi Maeda, Kyoto (JP); Takeshi Honda, Kyoto (JP); Nobuyuki Kita, Kyoto (JP)

(73) Assignees: NIDEC-SHIMPO CORPORATION, Kyoto (JP); NIDEC CORPORATION, Kyoto (JP)

(*) Notice: Subject to any disclaimer, the term of this patent is extended or adjusted under 35 U.S.C. 154(b) by 693 days.

(21) Appl. No.: 15/204,062

(22) Filed: Jul. 7, 2016

(65) Prior Publication Data
US 2017/0036261 A1 Feb. 9, 2017

Related U.S. Application Data

(60) Provisional application No. 62/189,328, filed on Jul. 7, 2015.

(51) Int. Cl.
*B21D 55/00* (2006.01)
*B21D 22/02* (2006.01)
(Continued)

(52) U.S. Cl.
CPC ............ *B21D 55/00* (2013.01); *B21D 22/02* (2013.01); *B21D 28/24* (2013.01); *G01L 5/0076* (2013.01);
(Continued)

(58) Field of Classification Search
CPC ........ B21D 22/02; B21D 28/24; B21D 55/00; G01L 5/0076; G01N 2291/0234;
(Continued)

(56) References Cited

U.S. PATENT DOCUMENTS

2004/0249611 A1 12/2004 Murao et al.
2007/0090098 A1* 4/2007 Murao .................. B23K 26/03
219/121.63

FOREIGN PATENT DOCUMENTS

CN 1352586 A 6/2002
CN 104190802 A 12/2014
(Continued)

OTHER PUBLICATIONS

Murao et al., "Improving Quality and Productivity through Newly Developed Acoustic Emissions Technology", Denso Technical Review, vol. 9, No. 1, 2004, pp. 92-99.

*Primary Examiner* — John H Le
(74) *Attorney, Agent, or Firm* — Keating & Bennett, LLP

(57) ABSTRACT

Provided is an abnormality prediction system and an abnormality prediction method that are capable of predicting an abnormality occurring in a die that is used in a press machine. A die abnormality prediction system (50) includes: an acoustic emission (AE) sensor (62) configured to detect an elastic wave that occurs in a processing portion of a die during processing performed by a press machine using the die; a stamping load detection sensor (61) configured to detect a parameter (a stamping load) other than a parameter regarding the elastic wave, out of parameters regarding a state of the die during the processing performed by the press machine using the die; a score calculation unit (56) configured to calculate an abnormality prediction score of the die based on an output signal from the AE sensor (62) and an output signal from the stamping load detection sensor (61); and an abnormality prediction unit (57) configured to predict (Continued)

an abnormality occurring in the die, based on a result of the calculation performed by the score calculation unit (56).

15 Claims, 8 Drawing Sheets

(51) Int. Cl.
      *G01N 29/44*     (2006.01)
      *G01L 5/00*     (2006.01)
      *G01N 29/14*     (2006.01)
      *G01N 29/04*     (2006.01)
      *B21D 28/24*     (2006.01)

(52) U.S. Cl.
    CPC .............. *G01N 29/04* (2013.01); *G01N 29/14* (2013.01); *G01N 29/4472* (2013.01); *G01N 2291/0234* (2013.01); *G01N 2291/0289* (2013.01); *G01N 2291/2698* (2013.01)

(58) Field of Classification Search
    CPC ... G01N 2291/0289; G01N 2291/2698; G01N 29/04; G01N 29/14; G01N 29/4472
    USPC ..... 702/35, 70, 71, 185; 219/121.62, 121.63
    See application file for complete search history.

(56) References Cited

FOREIGN PATENT DOCUMENTS

| | | |
|---|---|---|
| JP | 03-204155 A | 9/1991 |
| JP | 2001-047148 A | 2/2001 |
| JP | 2006-250236 A | 9/2006 |
| JP | 4372458 B2 | 11/2009 |
| JP | 4959360 B2 | 6/2012 |

\* cited by examiner

DIE ABNORMALITY PREDICTION SYSTEM, PRESS MACHINE PROVIDED WITH THE SAME, AND DIE ABNORMALITY PREDICTION METHOD

BACKGROUND OF THE INVENTION

1. Field of the Invention

The present invention relates to a die abnormality prediction system, a press machine provided with the same, and a die abnormality prediction method.

2. Description of Related Art

Regarding a press machine that performs stamping using a die, there is a conventionally known method for detecting an abnormality in the die. For example, Japanese Patent No. 4372458, Japanese Patent No. 4959360, and Masuaki MURAO, et al., "Improving Quality and Productivity through Newly Developed Acoustic Emissions Technology", Denso technical review, Vol. 9, No. 1, 2004, p. 92 to 99 disclose methods for detecting an abnormality during deformation processing, using an acoustic emission (AE) sensor that detects elastic waves generated from a processing portion of the die.

Japanese Patent No. 4372458, and Masuaki MURAO, et al., "Improving Quality and Productivity through Newly Developed Acoustic Emissions Technology", Denso technical review, Vol. 9, No. 1, 2004, p. 92 to 99, disclose an abnormality determination and evaluation method for determining a failure regarding a nick in a stamped product, and failures regarding a damage and an abrasion to a die, using elastic waves detected by an AE sensor.

Specifically, according to the method disclosed in Japanese Patent No. 4372458, abnormality determination is performed using, out of elastic waves detected by the AE sensor, first elastic waves that are emitted during a processing step that is performed immediately before an upper die is brought into contact with a lower die, second elastic waves that are emitted during a processing step that is performed when the upper die is brought into contact with the lower die, and third elastic waves that are emitted during a processing step performed after the upper die has brought into contact with the lower die. According to the method disclosed in the aforementioned Japanese Patent No. 4372458, a failure regarding a nick in a stamped product is determined based on the integrated value of the first elastic waves, and a failure regarding a damage to the die is determined based on the maximum value of the second elastic waves, and a failure regarding an abrasion to the die is determined based on the integrated value of the third elastic waves.

Japanese Patent No. 4959360 discloses a method for detecting an abnormality in deformation processing based on a value (power) obtained by analyzing the frequencies of elastic waves detected by an AE sensor.

Specifically, according to the method disclosed in Japanese Patent No. 4959360, the output signal from the AE sensor is also subjected to time-series frequency analysis per unit time, and power corresponding to the frequency is calculated in time-series per unit time. According to the method disclosed in Japanese Patent No. 4959360, an abnormality in deformation processing is detected by obtaining power differences between an obtained calculation value and reference data indicating time-series variations in the power corresponding to a frequency during normal deformation processing, and then using an integrated power difference per unit time obtained by calculating the sum of the power differences corresponding to the frequencies.

As disclosed in the above-described Japanese Patent No. 4372458, Japanese Patent No. 4959360, and Masuaki MURAO, et al., "Improving Quality and Productivity through Newly Developed Acoustic Emissions Technology", Denso technical review, Vol. 9, No. 1, 2004, p. 92 to 99, it is possible to detect an abnormality in stamping such as abrasion to a die by detecting elastic waves generated during stamping, using an AE sensor.

As described above, it is possible to determine whether or not an abnormality has occurred, using elastic waves detected by the AE sensor. However, in cases where processing is performed using a press machine or the like, even if a countermeasure such as die maintenance or die replacement is taken immediately after an abnormality is detected, there is the possibility of defective products being produced until the countermeasure is complete. As a result, it becomes necessary to perform a product test to determine whether or not products are defective and to discard defective products, and thus an additional cost is generated.

Therefore, it is important to determine when in the future an abnormality will occur in stamping, i.e., to determine the current state of stamping and to predict an abnormality that might occur in the future. By predicting the occurrence of an abnormality in such a manner, it is possible to promptly take a countermeasure such as die replacement, and it is therefore possible to prevent defective products from being wastefully produced.

SUMMARY OF THE INVENTION

The present invention aims to provide a system and a method that are capable of predicting an abnormality occurring in a die that is used in a press machine.

A die abnormality prediction system according to one aspect of the present invention is a die abnormality prediction system for predicting an abnormality in a die that is used in a press machine. This die abnormality prediction system includes: an acoustic emission (AE) sensor configured to detect an elastic wave that occurs in a processing portion of the die during stamping performed by the press machine using the die; a stamping state detection unit configured to detect a parameter other than a parameter regarding the elastic wave, out of parameters regarding a state of the die during the stamping performed by the press machine using the die; a score calculation unit configured to calculate an abnormality prediction score of the die based on an output signal from the AE sensor and an output signal from the stamping state detection unit; and an abnormality prediction unit configured to predict an abnormality occurring in the die, based on a result of the calculation performed by the score calculation unit.

A die abnormality prediction method according to another aspect of the present invention is a die abnormality prediction method for predicting an abnormality in a die that is used in a press machine. This die abnormality prediction method includes: an elastic wave component obtaining step of detecting, using an acoustic emission (AE) sensor, an elastic wave that occurs in a processing portion of the die during stamping performed by the press machine using the die, and obtaining a value regarding the elastic wave based on an output signal from the AE sensor; a die state component obtaining step of detecting, using a stamping state detection unit, a parameter other than a parameter regarding the elastic wave, out of parameters regarding a state of the die during the stamping performed by the press machine using the die, and obtaining a value regarding the state of the die based on the output signal from the stamping state detection unit; a score calculation step of calculating an abnormality prediction score of the die based on the value obtained in the elastic wave component obtaining step and the value obtained in the die state component obtaining step; and an abnormality prediction step of predicting an abnormality occurring in the die, based on a result of the calculation performed in the score calculation step.

With the die abnormality prediction system and the die abnormality prediction method according to aspects of the present invention, it is possible to realize an abnormality prediction system and an abnormality prediction method that are capable of predicting an abnormality occurring in a die.

DETAILED DESCRIPTION OF THE INVENTION

Figure 1:
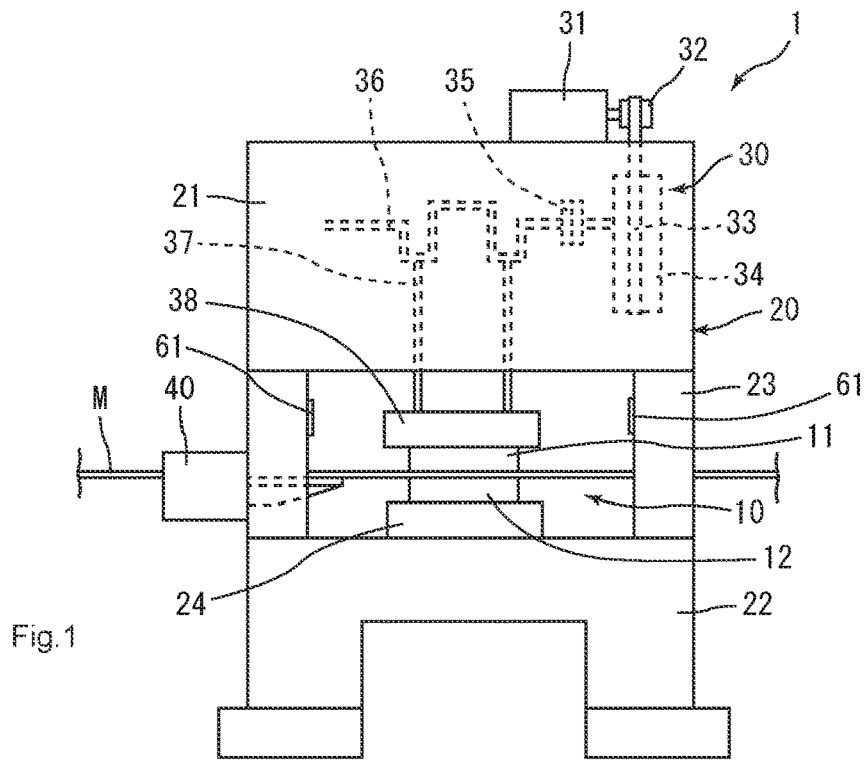
FIG. 1 is a front view showing a schematic configuration of a press machine that is provided with a die abnormality prediction system according to Embodiment 1 or 2.

The following describes embodiments of the present invention in detail with reference to the drawings. Note that the same or equivalent parts in the drawings are given the same reference numerals, and the description thereof is not repeated. Also note that the sizes of the components in each drawing do not faithfully represent the sizes of the actual components, the size ratio between the components, or the like.

In the following description, the vertical direction in the situation where a press machine 1 has been installed is referred to as "the top-bottom direction". The top-bottom direction coincides with the direction in which stamping using a die is performed. Also, in the situation where the press machine 1 has been installed, the left-right direction when the press machine 1 is seen from the front side is referred to as "the width direction".

Embodiment 1

Press Machine

FIG. 1 is a front view showing a schematic configuration of the press machine 1 according to an embodiment of the present invention. The press machine 1 is a processing machine that stamps a plate material M made of metal, using a die 10. The press machine 1 includes the die 10, a frame 20, a driving mechanism 30, a feeding device 40, and a die abnormality prediction system 50 (a system for predicting an abnormality in a die, see FIG. 3). FIG. 1 is a front view of the press machine 1.

The frame 20 includes a crown 21, a bed 22, and columns 23. The crown 21 and the bed 22 are connected to each other by the plurality of columns 23 located between them. In other words, the plurality of columns 23 support the crown 21 relative to the bed 22 at their four corners. The driving mechanism 30 is housed within the crown 21. A bolster 24 is located on the bed 22. The die 10 is fixed onto the bolster 24.

The feeding device 40 for conveying the plate material M from the outside of the press machine 1 toward the right in a front view of the press machine 1 is located on a side of the press machine 1. The feeding device 40 conveys the plate material M in the above-described manner, and thus the plate material M is continuously supplied to the die 10. Therefore, it is possible to continuously stamp the plate material M using the die 10. Note that the feeding device 40 is fixed to the columns 23.

The columns 23 are provided with a stamping load detection sensor 61 (a force sensor) that detects a stamping load that is applied when the press machine 1 performs stamping. Examples of the stamping load detection sensor 61 include a strain gauge. The stamping load detection sensor 61 constitutes a part of the die abnormality prediction system 50 described below.

The driving mechanism 30 is configured to be able to move an upper die 11 of the die 10 in the top-bottom direction. The upper die 11 will be described below. Specifically, the driving mechanism 30 includes a motor 31, a wheel 32, a belt 33, a flywheel 34, a clutch brake 35, a crankshaft 36, connecting rods 37, and a slide 38.

The motor 31 is located on the crown 21. The wheel 32 has a circular tube shape or a columnar shape, and is connected to the rotation shaft of the motor 31 such that the central axis of the wheel 32 coincides with the axis of the rotation shaft of the motor 31. With this configuration, the wheel 32 rotates integrally with the rotation shaft of the motor 31.

The belt 33 is wound around the wheel 32 and the flywheel 34 such that the belt 33 is located on the outer circumferential surface of the wheel 32 and the outer circumferential surface of the flywheel 34 that is located within the crown 21 and has a circular tube shape or a columnar shape. Using the belt 33, it is possible to transmit the rotation of the wheel 32 to the flywheel 34.

The crankshaft 36 is connected to the flywheel 34 such that the crankshaft 36 rotates integrally with the flywheel 34. Specifically, the crankshaft 36 is located within the crown 21 so as to extend in the width direction of the press machine 1, and one end of the crankshaft 36 is connected to the flywheel 34. Two connecting rods 37 are connected to the crankshaft 36 at different positions in terms of the direction in which the crankshaft 36 extends.

The respective front ends of the two connecting rods 37 are connected to the slide 38. Although not specifically shown in the drawings, the slide 38 is configured to be able to slide in the top-bottom direction relative to the frame 20. The upper die 11 is fixed to the bottom side of the slide 38.

Since the press machine 1 has the above-described configuration, the slide 38 slides in the top-bottom direction due to the rotation of the motor 31. The upper die 11 of the die 10 moves in the top-bottom direction due to the sliding of the slide 38. With this configuration, it is possible to sandwich the plate material M between the upper die 11 and a lower die 17, and to stamp the plate material M.

Die

Figure 2:
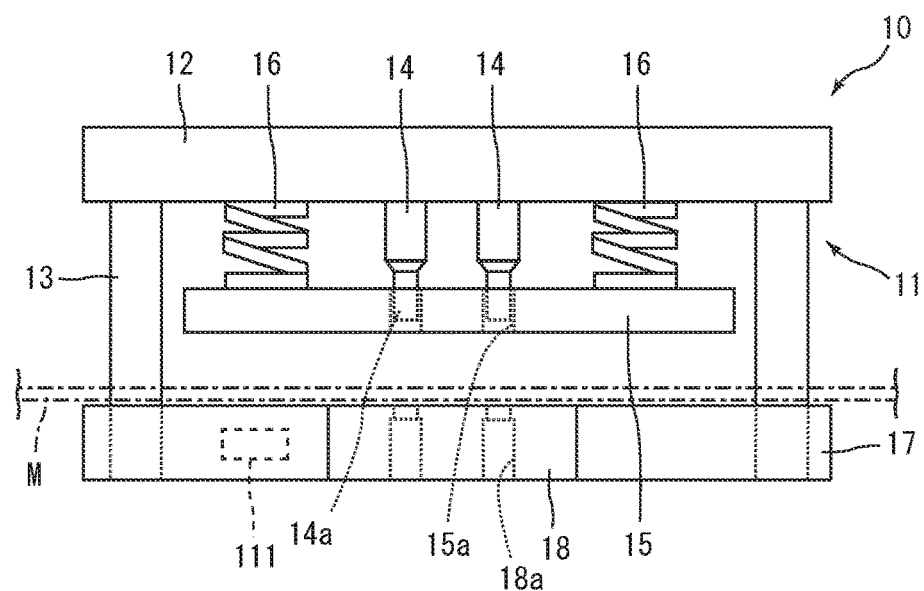
FIG. 2 is a front view showing a schematic configuration of a die.

Next, a configuration of the die 10 will be described with reference to FIG. 2.

The die 10 includes the upper die 11 and the lower die 17. The upper die 11 is configured to be able to slide in the top-bottom direction relative to the lower die 17. The die 10 is used for, for example, punching by which a predetermined shape is punched out of the plate material M. Therefore, the upper die 11 of the die 10 includes punches 14 and a stripper plate 15, which are described below.

Specifically, the upper die 11 includes a fixed-side attachment plate 12, guide pins 13, the punches 14, the stripper plate 15, and springs 16.

The fixed-side attachment plate 12 is, for example, a plate member that is made of metal and has a rectangular shape in plan view. The fixed-side attachment plate 12 is fixed to the lower surface of the slide 38 of the press machine 1.

The guide pins 13 respectively extend downward from the four corners of the lower surface of the fixed-side attachment plate 12. The lower ends of the guide pins 13 are respectively inserted into insertion holes (not shown) formed in the four corners of the lower die 17.

The respective front ends of the punches 14 have a tooth 14a for punching the plate material M. The punches 14 respectively extend downward from the lower surface of the fixed-side attachment plate 12. The teeth 14a are located on the lower side of the punches 14.

The stripper plate 15 is a plate member made of metal. The stripper plate 15 is connected to the fixed-side attachment plate 12 with the plurality of springs 16 interposed therebetween. Through holes 15a that respectively correspond to the punches 14 are formed in the stripper plate 15.

The springs 16 elastically support the stripper plate 15 such that the stripper plate 15 is parallel to the fixed-side attachment plate 12 and the front end portions of the punches 14 are located within the through holes 15a. The springs 16 are compression springs that generate elastic restoring force when being compressed in the direction in which the springs 16 expand or contract.

The lower die 17 is a flat member made of metal. The lower die 17 is provided with a die block 18 that corresponds to the punches 14 of the upper die 11. Through holes 18a that respectively correspond to the teeth 14a of the punches 14 are formed in the die blocks 18. A predetermined shape is punched out of the plate material M by the upper openings of the through holes 18a and the teeth 14a of the punches 14. The teeth 14a of the punches 14 enter the through holes 18a after the upper die 11 moves downward and the plate material M is punched by the punches 14.

The lower die 17 is provided with a bottom dead center detection sensor 111 for detecting the lowest position (the bottom dead center) of the stripper plate 15 of the upper die 11.

Die Abnormality Prediction System

Figure 3:
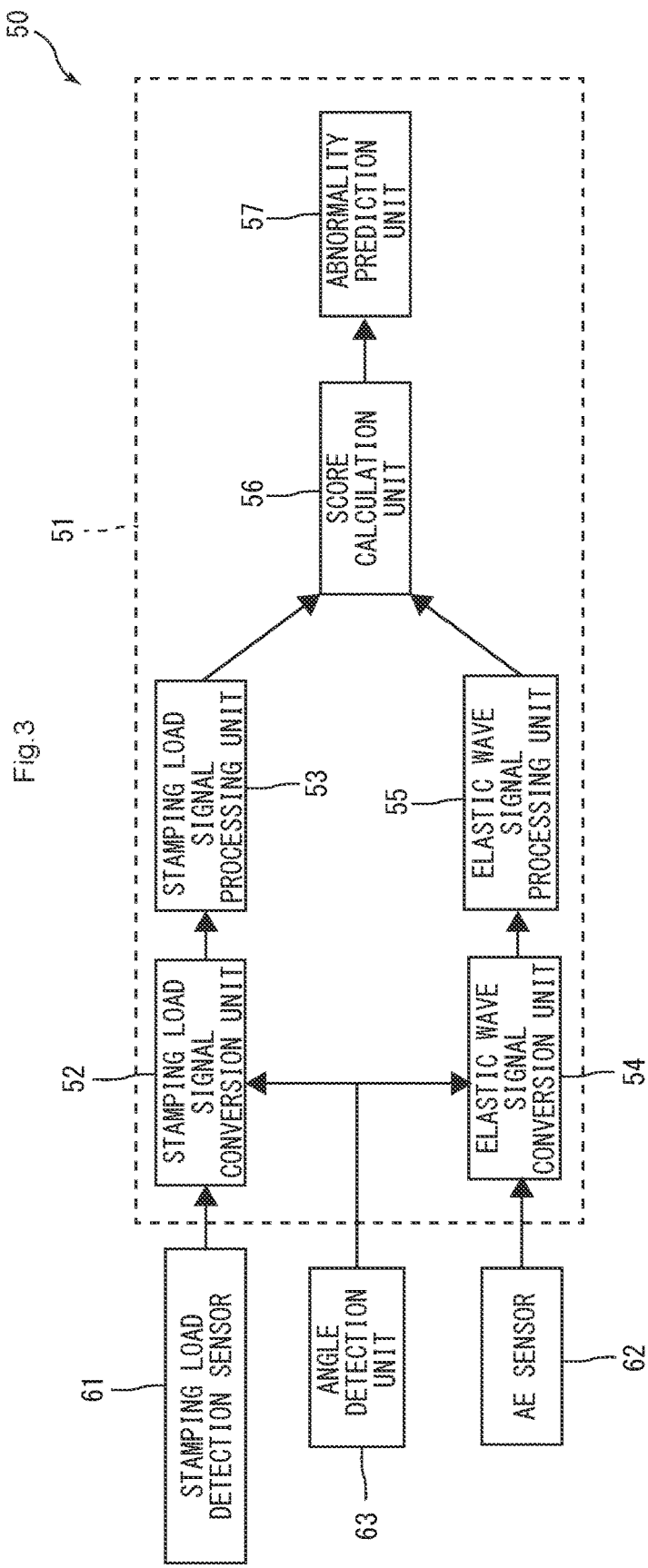
FIG. 3 is a block diagram showing a schematic configuration of a die abnormality prediction system according to Embodiment 1.
Figure 4:
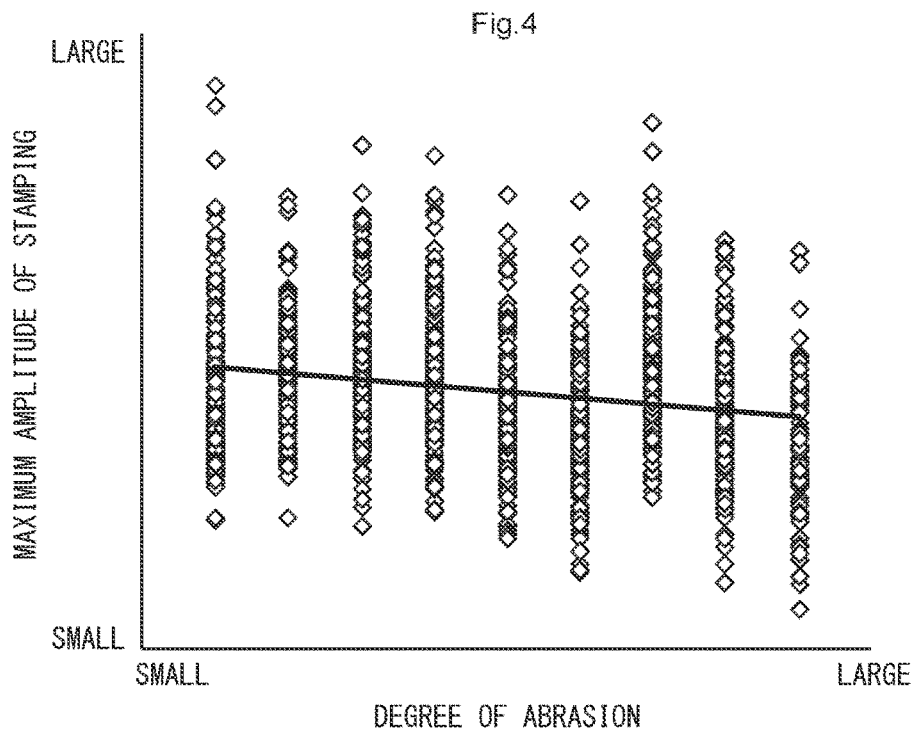
FIG. 4 is a diagram showing an example of a relationship between a stamping load and the degree of abrasion to the die.
Figure 5:
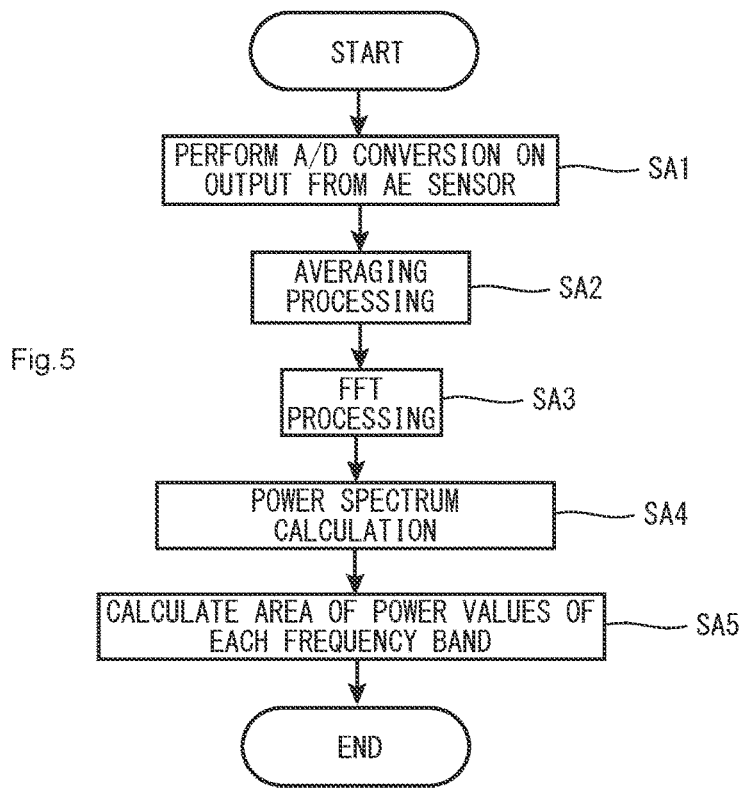
FIG. 5 is a flowchart illustrating the operation of a processing unit in the die abnormality prediction system.
Figure 6:
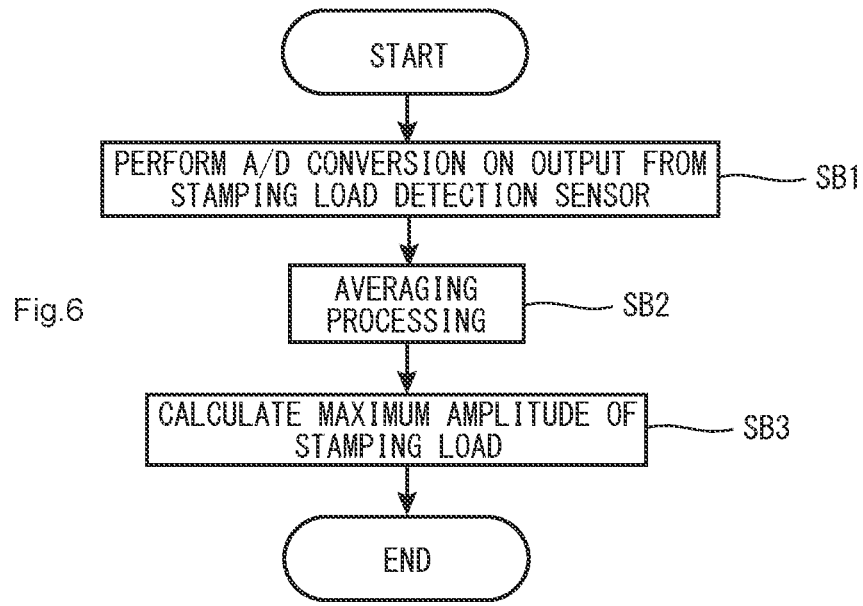
FIG. 6 is a flowchart illustrating the operation of the processing unit in the die abnormality prediction system.
Figure 7:
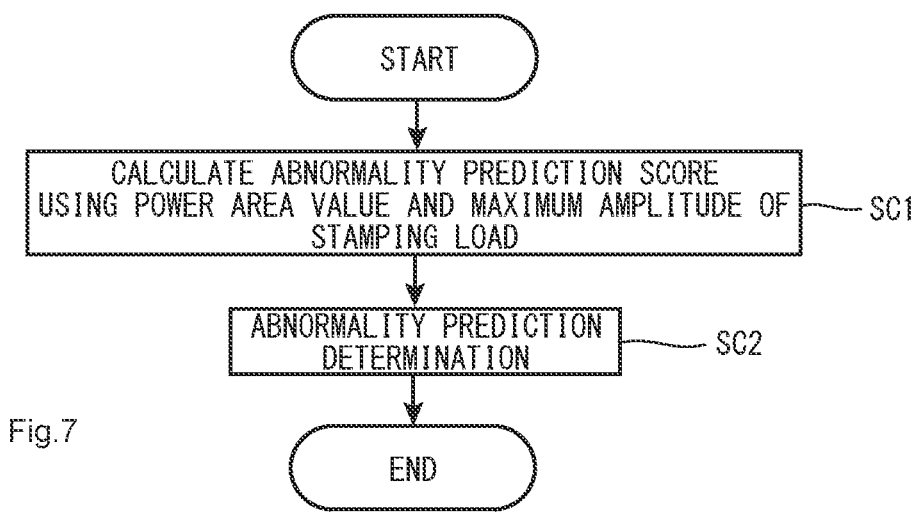
FIG. 7 is a flowchart illustrating the operation of the processing unit in the die abnormality prediction system.

Next the die abnormality prediction system 50 provided in the press machine 1 will be described with reference to FIGS. 3 to 7. FIG. 3 is a block diagram showing a schematic configuration of the die abnormality prediction system 50. FIG. 4 shows a relationship between the stamping load and the degree of abrasion to the die 10. FIGS. 5 to 7 show flowcharts illustrating the operation of the die abnormality prediction system 50.

The die abnormality prediction system 50 is a system for predicting an abnormality in the die 10 that is used when stamping the plate material M using the press machine 1. The die abnormality prediction system 50 may be provided in a control device (not shown) of the press machine 1, or in a control device that is provided separately from the press machine 1.

The die abnormality prediction system 50 estimates the current degree of abrasion to the die 10 by using elastic waves generated from a processing portion of the die 10 during stamping and a stamping load applied to the press machine 1 during stamping, and predicts an abnormality occurring in the die 10 (the occurrence of defective products due to abrasion) based on the degree of abrasion.

Specifically, as shown in FIG. 3, the die abnormality prediction system 50 includes a processing unit 51, the stamping load detection sensor 61 (a stamping state detection unit, a force sensor), an AE sensor 62, and an angle detection unit 63.

The stamping load detection sensor 61, when the press machine 1 performs stamping using the die 10, detects the stamping load (a parameter other than parameters regarding elastic waves, out of the parameters regarding the state of the die 10) that is generated in the columns 23 of the press machine 1. The AE sensor 62, when the press machine 1 performs stamping using the die 10, detects elastic waves that are generated in the processing portion of the die 10. The value detected by the stamping load detection sensor 61 and the value detected by the AE sensor 62 are output to the processing unit 51 as a stamping load signal and an elastic wave signal, respectively. Note that the stamping load signal and the elastic wave signal correspond to output signals.

The angle detection unit 63 detects the position, in terms of an angle, of the upper die 11 relative to the top-bottom direction of the press machine 1. Specifically, the angle detection unit 63 detects the position, in the top-bottom direction, of the slide 38 to which the upper die 11 is fixed, and converts the position of the slide 38 in the top-bottom direction into an angle, where the angle when the slide 38 moves back and forth once in the top-bottom direction is defined as 360°. Therefore, the angle when the slide 38 is located at the uppermost position in the top-bottom direction is defined as 0° or 360°, and the angle when the slide 38 is located at the lowermost position is defined as 180°. The angle detection unit 63 outputs such an angle signal. The angle signal output from the angle detection unit 63 is input to the processing unit 51.

Although not specifically shown in the drawings, the AE sensor 62 is located in the vicinity of the die 10 or is attached to the die 10. Although not specifically shown in the drawings, the angle detection unit 63 is located at a position where the angle detection unit 63 can detect the up-and-down movement of the slide 38 or the rotation of the crankshaft 36.

The processing unit 51 calculates an abnormality prediction score for estimating the degree of abrasion to the die 10 by using the stamping load signal and the elastic wave signal output from the stamping load detection sensor 61 and the AE sensor 62, and predicts an abnormality occurring in the die 10 by using the abnormality prediction score.

Specifically, the processing unit 51 includes a stamping load signal conversion unit 52, a stamping load signal processing unit 53, an elastic wave signal conversion unit 54, an elastic wave signal processing unit 55, a score calculation unit 56, and an abnormality prediction unit 57.

The stamping load signal conversion unit 52 converts, out of stamping load signals output from the stamping load detection sensor 61, only a stamping load signal corresponding to a desired angle within an angular range of a single shot (a single instance of stamping), from an analogue signal to a digital signal (hereinafter simply referred to as "A/D conversion"), where the angle is indicated by the angle signal obtained by the angle detection unit 63. Then, the stamping load signal conversion unit 52 extracts signals output during the period for which the plate material M is stamped using the die 10, and performs averaging processing on the signals to obtain an average with respect to a predetermined number of shots (a predetermined number of instances of stamping).

Note that the desired angle may be, within an angular range of a single shot of stamping, an angle indicating that the die 10 and the plate material M are in contact with each other, or an angle that is in synchronization with an angle of an elastic wave signal that is detected by the AE sensor 62.

The stamping load signal processing unit 53 obtains the maximum amplitude of the stamping load, using the signals that have undergone the averaging processing performed by the stamping load signal conversion unit 52.

Here, the stamping load signal is a signal that shows an increase in the stamping load when the plate material M is stamped using the die 10, and shows a decrease in the stamping load after the stamping is complete. For example, in the case where the stamping is punching, the stamping load signal indicates the maximum stamping load value when the punches 14 of the upper die 11 together with the die blocks 18 of the lower die 17 punch the plate material M therebetween, and the stamping load signal indicates the minimum stamping load value immediately after the punches 14 have punched the plate material M. The maximum amplitude is the difference between the maximum value and the minimum value of the stamping load in the case of stamping using the die 10.

As a result of a diligent effort, the inventors of the present invention found that the degree of abrasion to the die and the maximum amplitude of the stamping load are correlative as shown in FIG. 4. FIG. 4 shows an example of a relationship between the degree of abrasion to the die and the maximum amplitude of the stamping load. As can be seen from FIG. 4, the degree of abrasion to the die tends to increase as the maximum amplitude of the stamping load decreases.

The inventors focused on the aforementioned relationship between the degree of abrasion to the die and the maximum amplitude of the stamping load, and conceived of using the stamping load to estimate the degree of abrasion to the die. Specifically, as described below, the die abnormality prediction system 50 according to the present embodiment uses the output signal from the stamping load detection sensor 61 to calculate the abnormality prediction score, and predicts an abnormality occurring in the die 10 based on the current degree of abrasion to the die 10 by using the abnormality prediction score.

The elastic wave signal conversion unit 54 performs A/D conversion on, out of elastic wave signals output from the AE sensor 62, only an elastic wave signal corresponding to a desired angle within an angular range of a single shot (a single instance of stamping), where the angle is indicated by the angle signal obtained by the angle detection unit 63. Then, the elastic wave signal conversion unit 54 extracts signals output during the period for which the plate material M is stamped using the die 10, and performs averaging processing on the signals to obtain an average with respect to a predetermined number of shots. Then, the elastic wave signal conversion unit 54 performs fast Fourier transform (hereinafter simply referred to as "FFT processing") and a power spectrum calculation on the signals that have undergone averaging processing, to obtain the respective power values of the frequency bands.

Note that the desired angle may be, within an angular range of a single shot of stamping, an angle indicating that the die 10 and the plate material M are in contact with each other, or an angle that is in synchronization with an angle of the stamping load signal that is detected by the stamping load detection sensor 61.

The elastic wave signal processing unit 55 calculates the values of features of the frequency bands, using the respective power values of the frequency bands, obtained by the elastic wave signal conversion unit 54. For example, the elastic wave signal processing unit 55 performs an area calculation (a calculation for obtaining the integral of the power values in a frequency band). The elastic wave signal processing unit 55 performs the aforementioned power value area calculation for each predetermined frequency band (e.g. per 100 kHz). Note that examples of the values of features of the frequency bands include an average value in a frequency band, in addition to the aforementioned area.

The score calculation unit 56 calculates the abnormality prediction score of the die 10 based on the respective output signals from the AE sensor 62 and the stamping load detection sensor 61. In other words, the score calculation unit 56 calculates the abnormality prediction score, using the maximum amplitude of the stamping load obtained by the stamping load signal processing unit 53, and the area of the respective power values of the frequency bands (power area value), obtained by the elastic wave signal processing unit 55. Specifically, the score calculation unit 56 calculates the abnormality prediction score by assigning a weight to the maximum amplitude and to the power area value and obtaining the sum of the obtained values.

More specifically, the score calculation unit 56 calculates a corrected maximum amplitude value by multiplying the maximum amplitude, which has been obtained by the stamping load signal processing unit 53, by a stamping load coefficient. The score calculation unit 56 also calculates a corrected elastic wave value by multiplying the respective power area values of the frequency bands, which have been obtained by the elastic wave signal processing unit 55, by an elastic wave coefficient, and obtaining the sum of the resultant values. Then, the score calculation unit 56 obtains the sum of the corrected maximum amplitude value and the corrected elastic wave value as the abnormality prediction score.

The score calculation unit 56 calculates the abnormality prediction score P by using the following equation, for example.

$$P = \Sigma(Kn \times Sn) + (M \times L_{p-p})$$

Here, $Kn$ denotes the elastic wave coefficient, which is set for each frequency band. $Sn$ denotes the area of the respective power values of the frequency bands. $M$ denotes the stamping load coefficient, and $L_{p-p}$ denotes the maximum amplitude of the stamping load.

The elastic wave coefficient and the stamping load coefficient are set according to the respective degrees of contribution of the elastic wave and the maximum amplitude of the stamping load to the degree of abrasion to the die 10. The elastic wave coefficient is set such that the degree of contribution of the power values of high frequency bands (e.g. 500 kHz or higher), in which the power value is relatively small, is adjusted relative to the power values of low frequency bands (e.g. 100 kHz or lower), in which the power value is relatively large. This is because, in elastic waves that are generated in the processing portion of the die 10, high frequency components significantly affect the prediction of an abnormality in the die 10.

Note that the elastic wave coefficient and the stamping load coefficient may be optimized by repeating the calculation of the abnormality prediction score and the prediction of the occurrence of an abnormality in the die 10, or performing the calculation of the abnormality prediction score and the prediction of the occurrence of an abnormality in the die 10 using a plurality of press machines 1.

Also, the score calculation unit 56 may calculate the abnormality prediction score using a method other than the above-described method. In other words, any calculation method may be adopted insofar as it is a method for calculating the abnormality prediction score taking the stamping load and the elastic waves into consideration.

The abnormality prediction unit 57 predicts an abnormality occurring in the die 10, using the abnormality prediction score calculated by the score calculation unit 56. Specifically, the abnormality prediction unit 57 displays the score value of the abnormality prediction score obtained by the score calculation unit 56, and notifies the operator of the timing of preparing for the replacement of the die 10, or the timing of replacing the die 10, for example, according to the score value. By making such a notification, it is possible to prevent a large number of defective products from being produced using a die that has been abraded, and it is possible to improve the productivity.

Next, the operation of the processing unit 51 of the die abnormality prediction system 50 having the above-described configuration will be described with reference to FIGS. 5 to 7. FIG. 5 is a flowchart showing a process in which the processing unit 51 calculates the power area value by using the elastic wave signal output from the AE sensor 62. FIG. 6 is a flowchart showing a process in which the processing unit 51 calculates the maximum amplitude of the stamping load by using the stamping load signal output from the stamping load detection sensor 61. FIG. 7 is a flowchart showing a process in which the abnormality prediction score is calculated using the power area value and the maximum amplitude of the stamping load, and the operation for abnormality prediction is performed based on the abnormality prediction score.

Upon the process shown in FIG. 5 being started, in step SA1, the elastic wave signal conversion unit 54 performs A/D conversion on an elastic wave signal output from the AE sensor 62, using the angle signal output from the angle detection unit 63. Specifically, the elastic wave signal conversion unit 54 performs A/D conversion on, out of elastic wave signals output from the AE sensor 62, only an elastic wave signal corresponding to a desired angle within an angular range of a single shot (a single instance of stamping), where the angle is indicated by the angle signal obtained by the angle detection unit 63. The desired angle may be, within an angular range of a single shot of stamping, an angle indicating that the die 10 and the plate material M are in contact with each other, or an angle that is in synchronization with an angle of the stamping load signal that is detected by the stamping load detection sensor 61.

In the subsequent step SA2, the elastic wave signal conversion unit 54 extracts, out of the signals that have undergone the A/D conversion, signals output during the period for which the plate material M is stamped using the die 10, and performs averaging processing on the signals to obtain an average with respect to a predetermined number of shots. Then, in steps SA3 and SA4, the elastic wave signal conversion unit 54 performs a power spectrum calculation by performing FFT processing on the signals that have undergone averaging processing.

In step SA5, the elastic wave signal processing unit 55 calculates the value of feature (e.g. the area of power values) of each frequency band using data resulting from the FFT processing and the power spectrum calculation. In the example shown in FIG. 5, the elastic wave signal processing unit 55 performs a calculation for obtaining the integral of power values, i.e., an area calculation, for each predetermined frequency band (e.g. per 100 kHz). Note that the elastic wave signal processing unit 55 may calculate, as the values of features of the frequency bands, an average value in each frequency band instead of the aforementioned area.

Subsequently, this process is ended (END).

Next, upon the process shown in FIG. 6 being started, in step SB1, the stamping load signal conversion unit 52 performs A/D conversion on stamping load signals output from the stamping load detection sensor 61, using the angle signal output from the angle detection unit 63. Specifically, the stamping load signal conversion unit 52 performs A/D conversion on, out of stamping load signals output from the stamping load detection sensor 61, only a stamping load signal corresponding to a desired angle within an angular range of a single shot (a single instance of stamping), where the angle is indicated by the angle signal obtained by the angle detection unit 63. The desired angle may be, within an angular range of a single shot of stamping, an angle indicating that the die 10 and the plate material M are in contact with each other, or an angle that is in synchronization with an angle of an elastic wave signal that is detected by the AE sensor 62.

In the subsequent step SB2, the stamping load signal conversion unit 52 extracts, out of the signals that have undergone the A/D conversion, signals output during the period for which the plate material M is stamped using the die 10, and performs averaging processing on the signals to obtain an average with respect to a predetermined number of shots.

Then, in step SB3, the stamping load signal processing unit 53 calculates the maximum amplitude of the stamping load, using the signals that have undergone averaging processing. Subsequently, this process is ended (END).

Upon the process shown in FIG. 7 being started, in step SC1, the score calculation unit 56 calculates the abnormality prediction score, using the area of power values (power area value) of each frequency band, obtained by the elastic wave signal processing unit 55, and the maximum amplitude of the stamping load, calculated by the stamping load signal processing unit 53. Specifically, the score calculation unit 56 obtains the corrected elastic wave value by multiplying the power area value by the elastic wave coefficient corresponding to the frequency band, and obtains the corrected maximum amplitude value by multiplying the maximum amplitude of the stamping load by the stamping load coefficient. Then, the score calculation unit 56 calculates the sum of the corrected elastic wave value and the corrected maximum amplitude value as the abnormality prediction score.

In the subsequent step SC2, the abnormality prediction unit 57 displays the score value of the abnormality prediction score obtained in step SC1, and notifies the operator of the timing of preparing for the replacement of the die 10, or the timing of replacing the die 10, for example, according to the score value. Subsequently, this process is ended (END).

The above-described steps SA1 to SA5 correspond to an elastic wave component obtaining step in which elastic waves generated in processing portion of the die 10 during the stamping performed by the press machine 1 using the die 10 are detected by the AE sensor 62, and values regarding the elastic waves (the areas of the respective power values of the frequency bands) are obtained based on the output signal from the AE sensor 62.

The above-described steps SB1 to SB3 correspond to a die state component obtaining step in which a parameter (a stamping load) other than parameters regarding elastic waves, out of the parameters regarding the state of the die 10 during the stamping performed by the press machine 1 using the die 10, is detected by the stamping load detection sensor 61, and a value regarding the state of the die 10 (the maximum amplitude of the stamping load) is obtained based on the output signal from the stamping load detection sensor 61.

The above-described step SC1 corresponds to a score calculation step in which the abnormality prediction score of the die 10 is calculated based on the value obtained in the elastic wave component obtaining step and the value obtained in the die state component obtaining step. The above-described step SC2 corresponds to an abnormality prediction step in which an abnormality occurring in the die 10 is predicted, based on the result of the calculation performed in the score calculation step.

Note that the score calculation unit 56 may simultaneously perform process to values obtained in FIGS. 5 and 6, or perform process to either one of the values first.

As described above, according to the present embodiment, during the stamping performed by the press machine 1 using the die 10, the die abnormality prediction system 50 detects elastic waves generated in the processing portion of the die 10, using the AE sensor 62, and detects the stamping load during the stamping, using the stamping load detection sensor 61. Then, the die abnormality prediction system 50 calculates the abnormality prediction score based on the elastic wave signal detected by the AE sensor 62 and the stamping load signal detected by the stamping load detection sensor 61, and predicts an abnormality occurring in the die 10, using the abnormality prediction score.

With conventional processing abnormality detection using only the AE sensor 62, although it is possible to detect the occurrence of an abnormality, it is not possible to detect the degree of abrasion to the die 10. Therefore, it is difficult to predict an abnormality occurring in the die 10.

In contrast, with the above-described configuration, it is possible to obtain the degree of abrasion to the die 10 by obtaining the abnormality prediction score, using the output signal indicating the stamping load detected by the stamping load detection sensor 61 in addition to the output signal indicating the elastic wave detected by the AE sensor 62. Therefore, it is possible to accurately detect the current state of the die 10, and accordingly it is possible to predict an abnormality occurring in the die 10. Thus, with the above-described configuration, it is possible to obtain a system that is capable of predicting an abnormality occurring in the die 10.

The score calculation unit 56 of the die abnormality prediction system 50 calculates weighted values by assigning a weight to the value calculated based on the output signal from the AE sensor 62 (the area of power values in each frequency band) and to the value calculated based on the output signal from the stamping load detection sensor 61 (the maximum amplitude of the stamping load), and obtains the sum of the weighted values as the abnormality prediction score.

It is possible to detect the state of the processing portion of the die 10 from the elastic wave detected by the AE sensor 62, and it is possible to detect the stamping state of the stamping using the die 10 from the stamping load detected by the stamping load detection sensor 61. Therefore, it is possible to obtain the abnormality prediction score that accurately reflects the state of the die 10, by assigning a weight to the obtained values corresponding to these state, based on the relationship between the values, and obtaining the sum of the resultant values. Therefore, it is possible to accurately predict an abnormality occurring in the die 10.

The above-described die abnormality prediction system 50 is suitable for predicting an abnormality occurring in the die 10 that is used for shearing. It is possible to accurately detect elastic waves generated in the processing portion of the die 10 used for shearing, using the AE sensor 62. Therefore, the above-described die abnormality prediction system 50 has a configuration that is effective for predicting an abnormality occurring in the die 10 used for shearing.

Also, the die abnormality prediction system 50 obtains the abnormality prediction score by calculating the sum of the corrected elastic wave value and the corrected maximum amplitude value, which have been obtained by assigning a weight to the area of power values in each frequency band, obtained from the output signal from the AE sensor 62, and to the maximum amplitude of the stamping load, obtained from the output signal from the stamping load detection sensor 61, by multiplying them by their respective predetermined coefficients. Thus, it is possible to accurately obtain the abnormality prediction score by using the signals detected by the AE sensor 62 and the stamping load detection sensor 61. Therefore, it is possible to accurately estimate the current degree of abrasion to the die 10, and it is possible to accurately predict an abnormality occurring in the die 10.

Note that in the present embodiment, the stamping load detection sensor 61 that detects the stamping load is used as a sensor for detecting the state of the die 10 during the stamping performed by the press machine 1. However, such a configuration is not essential, and it is also possible to use another sensor to detect force generated during stamping, other than the stamping load, and predict an abnormality occurring in the die 10 by using the output signal from the sensor.

Embodiment 2

Figure 8:
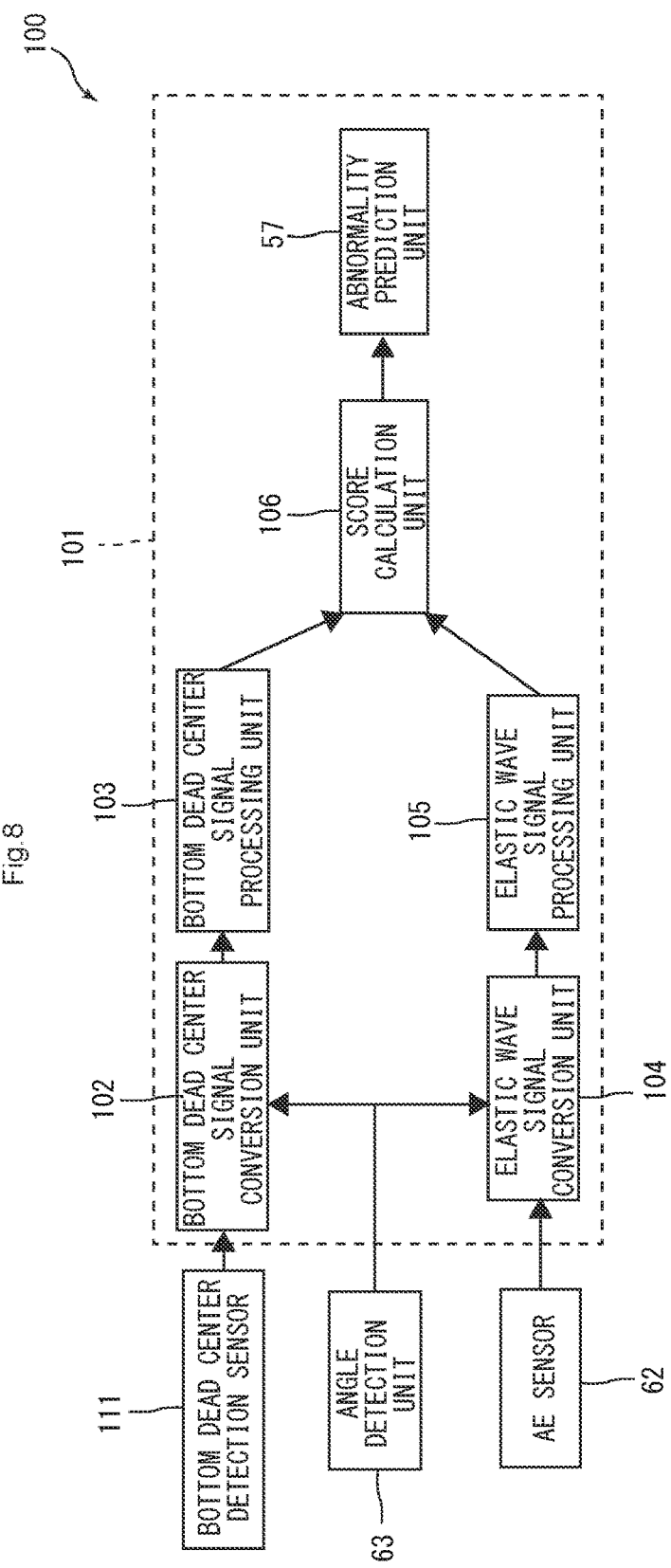
FIG. 8 is a block diagram showing a schematic configuration of a die abnormality prediction system according to Embodiment 2.

FIG. 8 is a block diagram showing a schematic configuration of a die abnormality prediction system 100 according to Embodiment 2. The configuration of the die abnormality prediction system 100 according to Embodiment 2 is different from the configuration according to Embodiment 1 in that the bottom dead center detection sensor 111 is used instead of the stamping load detection sensor 61. In the following description, the same components as in Embodiment 1 are given the same reference numerals as in Embodiment 1 and their description is omitted. The following describes only differences from Embodiment 1.

The die abnormality prediction system 100 includes a processing unit 101, the bottom dead center detection sensor 111, the AE sensor 62, and the angle detection unit 63. The bottom dead center detection sensor 111 (the stamping state detection unit, a die position detection sensor) detects the position (the position of the die) of the lowermost point (the bottom dead center) of the stripper plate 15 of the upper die 11 in the top-bottom direction of the press machine 1 (the direction in which stamping is performed), and outputs the result of detection as a bottom dead center signal. In other words, the bottom dead center detection sensor 111 detects a parameter (a bottom dead center) other than parameters regarding elastic waves, out of the parameters regarding the state of the die 10 during the processing performed by the press machine 1 using the die 10. As shown in FIG. 2, the bottom dead center detection sensor 111 is attached to the lower die 17.

The processing unit 101 calculates the abnormality prediction score for estimating the degree of abrasion to the die 10 by using the bottom dead center signal and the elastic wave signals from the bottom dead center detection sensor 111 and the AE sensor 62, and predicts an abnormality occurring in the die 10 by using the abnormality prediction score.

Specifically, the processing unit 101 includes a bottom dead center signal conversion unit 102, a bottom dead center signal processing unit 103, an elastic wave signal conversion unit 104, an elastic wave signal processing unit 105, a score calculation unit 106, and the abnormality prediction unit 57.

The bottom dead center signal conversion unit 102 performs A/D conversion on, out of bottom dead center signals output from the bottom dead center detection sensor 111, only a bottom dead center signal corresponding to a desired angle within an angular range of a single shot (a single instance of stamping), where the angle is indicated by the angle signal obtained by the angle detection unit 63.

The bottom dead center signal processing unit 103 extracts pieces of data corresponding to positions at or in the vicinity of the bottom dead center (a predetermined range of the bottom dead center in the top-bottom direction of the stripper plate 15) from the signals that have undergone the A/D conversion, and obtains the average of these pieces of data. The bottom dead center signal processing unit 103 also obtains a bottom dead center value (position data) by performing averaging processing on the obtained average value with respect to a predetermined number of shots.

Figure 9:
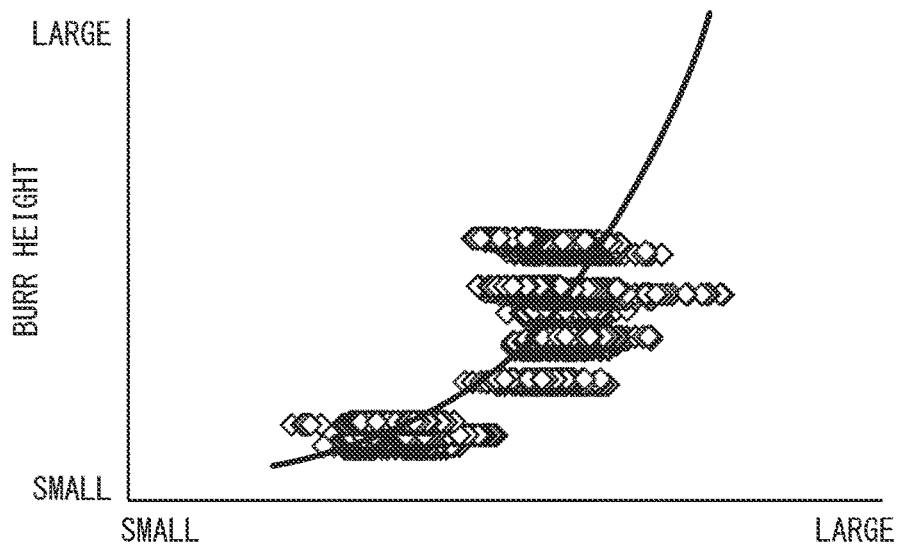
FIG. 9 is a diagram showing an example of a relationship between an output from a bottom dead center detection sensor and a burr height.

As a result of a diligent effort, the inventors of the present invention found that the bottom dead center signal and the height (hereinafter referred to as "the burr height") of a burr of the plate material stamped using the die 10 are correlative as shown in FIG. 9. That is, the output level of the bottom dead center signal increases as the burr height increases, and the output level of the bottom dead center signal decreases as the burr height decreases. Note that in the present embodiment, the position of the bottom dead center of the stripper plate 15 becomes higher as the output level of the bottom dead center signal increases.

It is known that the burr height usually increases as the degree of abrasion to the die 10 increases. Therefore, the bottom dead center signal and the amount of abrasion to the die 10 are correlative. The inventors focused on the fact that the bottom dead center signal and the amount of abrasion to the die 10 are correlative, and conceived of using the bottom dead center signal to estimate the degree of abrasion to the die 10. Specifically, as described below, the die abnormality prediction system 100 according to the present embodiment uses the result of detection by the bottom dead center detection sensor 111 to calculate the abnormality prediction score, and predicts an abnormality occurring in the die 10 based on the current degree of abrasion to the die 10 by using the abnormality prediction score.

The elastic wave signal conversion unit 104 performs A/D conversion on, out of elastic wave signals output from the AE sensor 62, only an elastic wave signal corresponding to a desired angle within an angular range of a single shot (a single instance of stamping), where the angle is indicated by the angle signal obtained by the angle detection unit 63. Then, the elastic wave signal conversion unit 104 extracts, from the signals that have undergone the A/D conversion, signals output during the period for which the plate material M is stamped using the die 10. Then, the elastic wave signal conversion unit 104 performs FFT processing and a power spectrum calculation on the extracted signals to obtain the respective power values of the frequency bands as functions of frequency.

The elastic wave signal processing unit 105 extracts, out of the respective power values of the frequency bands obtained by the elastic wave signal conversion unit 104, values within a predetermined frequency band (e.g. a range from 300 kHz to 500 kHz), and obtains the average of the extracted values. Then, the elastic wave signal processing unit 105 performs averaging processing on the obtained average value with respect to a predetermined number of shots to obtain an elastic wave power value.

The score calculation unit 106 calculates the abnormality prediction score of the die 10 based on the respective output signals from the AE sensor 62 and the bottom dead center detection sensor 111. In other words, the score calculation unit 106 calculates the abnormality prediction score by using the bottom dead center value obtained by the bottom dead center signal processing unit 103 and the elastic wave power value obtained by the elastic wave signal processing unit 105. Specifically, the score calculation unit 106 calculates the abnormality prediction score by assigning a weight to the bottom dead center value and to the elastic wave power value, and obtaining the sum of the obtained values.

Specifically, the score calculation unit 106 calculates a corrected bottom dead center value by multiplying the bottom dead center value obtained by the bottom dead center signal processing unit 103 by a bottom dead center coefficient. The score calculation unit 106 also calculates a corrected elastic wave power value by multiplying the elastic wave power value obtained by the elastic wave signal processing unit 105 by an elastic wave coefficient. Then, the score calculation unit 106 obtains the sum of the corrected bottom dead center value and the corrected elastic wave power value as the abnormality prediction score.

Here, the bottom dead center coefficient and the elastic wave coefficient have been set by the score calculation unit 106 such that when the degree of abrasion to the die 10 is within a predetermined range, the sum of the differences between the degree of abrasion described below and the abnormality prediction score has the minimum value. Note that the bottom dead center coefficient and the elastic wave coefficient may be fixed values or values that have been obtained based on an experiment or an experience insofar as these values can correct the differences between the degree of actual abrasion and the abnormality prediction score.

The score calculation unit 106 calculates the abnormality prediction score P by using the following equation, for example.

$$P = \Sigma(Kn \times Sn)$$

Here, Kn denotes a coefficient, and Sn denotes the value of the feature obtained based on the signals output from the sensors. In the case of using the signals output from a plurality of sensors as in the present embodiment, the value of the feature may be obtained by calculating the sum of the values resulting from multiplying predetermined coefficients to the values of features obtained based on the signals output from the plurality of sensors.

Figure 10:
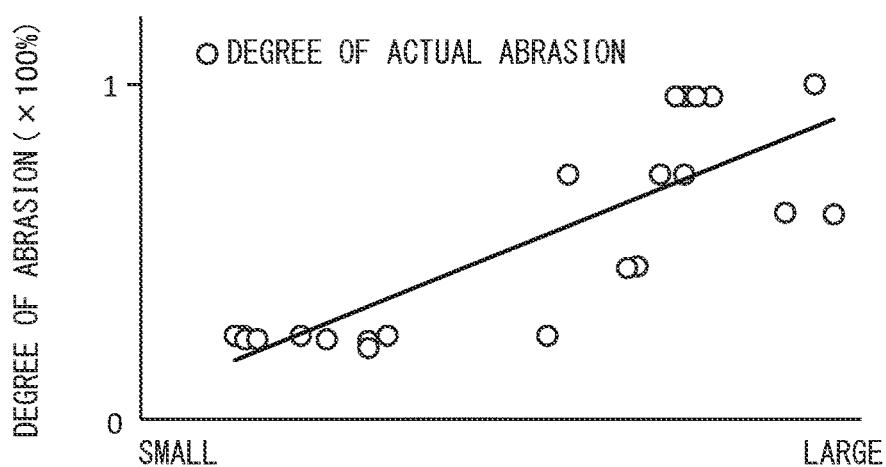
FIG. 10 is a diagram showing a relationship between a degree of abrasion and an abnormality prediction score.

The abnormality prediction score is correlative with the degree of actual abrasion as shown in FIG. 10. Specifically, the abnormality prediction score increases as the degree of actual abrasion increases. Note that the degree of abrasion shown in FIG. 10 (the open circles) were determined based on the height of burrs formed on the plate material stamped using the die 10. As described above, the degree of abrasion to the die increases as the burr height increases. Therefore, the degree of abrasion was calculated based on the ratio of the burr height to the reference value (the maximum acceptable burr height of a product).

Note that the score calculation unit 106 may calculate the abnormality prediction score using a method other than the above-described method. In other words, any calculation method may be adopted insofar as it is a method for calculating the abnormality prediction score taking the bottom dead center and the elastic waves into consideration.

The abnormality prediction unit 57 predicts an abnormality occurring in the die 10, using the abnormality prediction score calculated by the score calculation unit 106. The abnormality prediction unit 57 displays the score value of the abnormality prediction score obtained by the score calculation unit 106, and notifies the operator of the timing of preparing for the replacement of the die 10, or the timing of replacing the die 10, for example, according to the score value. By making such a notification, it is possible to prevent a large number of defective products from being produced using a die that has been abraded, and it is possible to improve the productivity.

Figure 11:
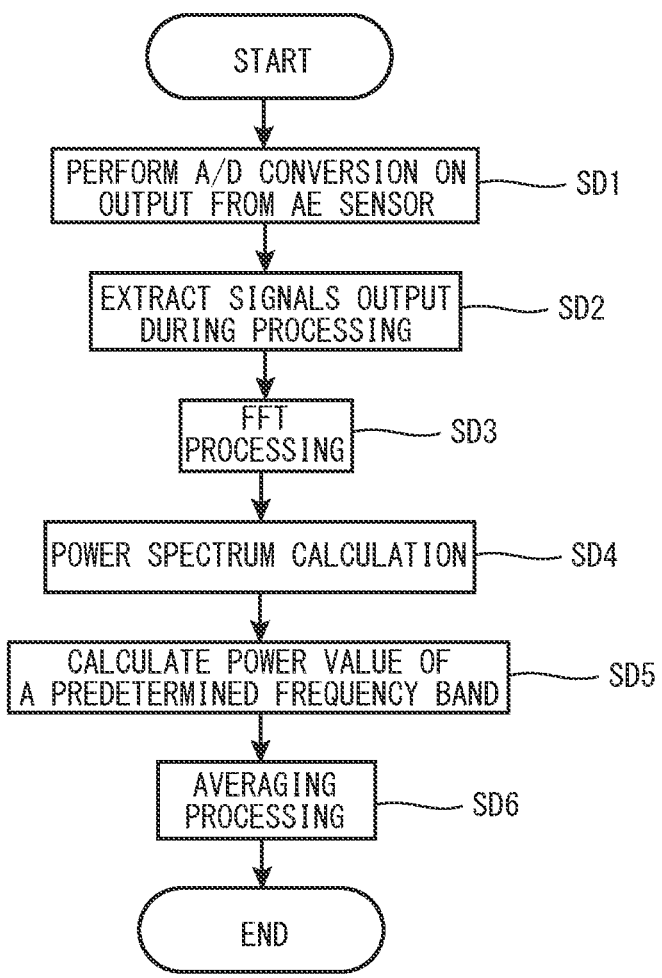
FIG. 11 is a flowchart illustrating the operation of the processing unit in the die abnormality prediction system.
Figure 12:
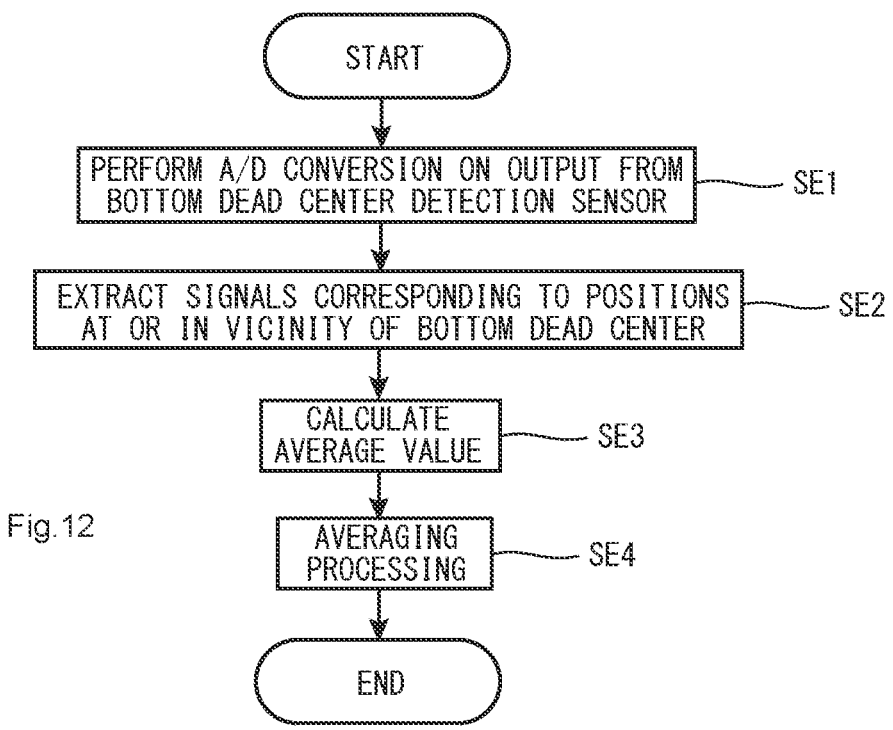
FIG. 12 is a flowchart illustrating the operation of the processing unit in the die abnormality prediction system.
Figure 13:
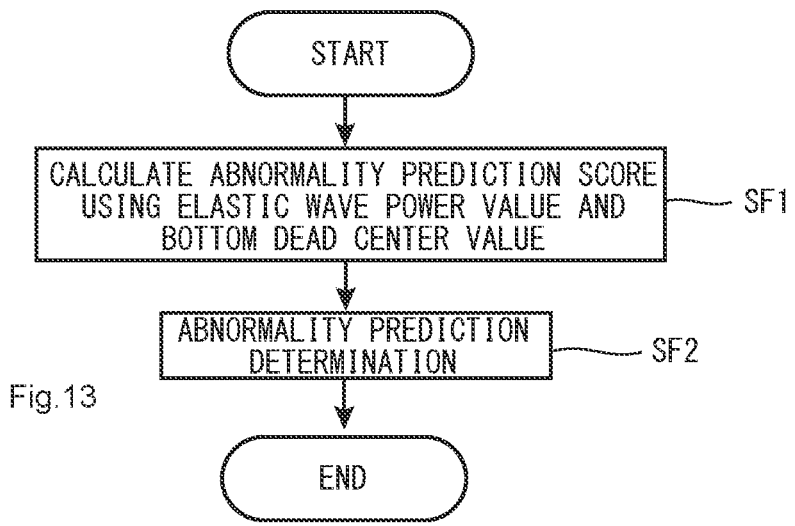
FIG. 13 is a flowchart illustrating the operation of the processing unit in the die abnormality prediction system.

Next, the operation of the processing unit 101 of the die abnormality prediction system 100 having the above-described configuration will be described with reference to FIGS. 11 to 13. FIG. 11 is a flowchart showing a process in which the processing unit 101 calculates the elastic wave power value by using the elastic wave signal output from the AE sensor 62. FIG. 12 is a flowchart showing a process in which the processing unit 101 calculates the bottom dead center value by using the bottom dead center signal output from the bottom dead center detection sensor 111. FIG. 13 is a flowchart showing a process in which the abnormality prediction score is calculated using the elastic wave power value and the bottom dead center value, and the operation for abnormality prediction is performed based on the abnormality prediction score.

Upon the process shown in FIG. 11 being started, in step SD1, the elastic wave signal conversion unit 104 performs A/D conversion on elastic wave signals output from the AE sensor 62, using the angle signal output from the angle detection unit 63. Specifically, the elastic wave signal conversion unit 104 performs A/D conversion on, out of elastic wave signals output from the AE sensor 62, only an elastic wave signal corresponding to a desired angle within an angular range of a single shot (a single instance of stamping), where the angle is indicated by the angle signal obtained by the angle detection unit 63. The desired angle may be, within an angular range of a single shot of stamping, an angle indicating that the die 10 and the plate material M are in contact with each other, or an angle that is in synchronization with an angle of a bottom dead center signal detected by the bottom dead center detection sensor 111.

In the subsequent step SD2, the elastic wave signal conversion unit 104 extracts, from the signals that have undergone the A/D conversion, signals output during the processing performed using the die 10. Then, in steps SD3 and SD4, the elastic wave signal conversion unit 104 performs a power spectrum calculation by performing FFT processing on the signals that have been extracted.

In step SD5, the elastic wave signal processing unit 105 calculates the average of the power values of the predetermined frequency band by using data that have undergone the FFT processing and the power spectrum calculation. In step SD6, the elastic wave signal processing unit 105 performs averaging processing on the average value with respect to a predetermined number of shots to calculate an elastic wave power value. Subsequently, this process is ended (END).

Next, upon the process shown in FIG. 12 being started, in step SE1, the bottom dead center signal conversion unit 102 performs A/D conversion on the bottom dead center signal output from the bottom dead center detection sensor 111, using the angle signal output from the angle detection unit 63. Specifically, the bottom dead center signal conversion unit 102 performs A/D conversion on, out of bottom dead center signals output from the bottom dead center detection sensor 111, only a bottom dead center signal corresponding to a desired angle within an angular range of a single shot (a single instance of stamping), where the angle is indicated by the angle signal obtained by the angle detection unit 63. The desired angle may be, within an angular range of a single shot of stamping, an angle indicating that the die 10 and the plate material M are in contact with each other, or an angle that is in synchronization with an angle of an elastic wave signal that is detected by the AE sensor 62.

In the subsequent step SE2, the bottom dead center signal processing unit 103 extracts pieces of data corresponding to positions at or in the vicinity of the bottom dead center (a predetermined range of the bottom dead center in the top-bottom direction of the stripper plate 15) from the signals that have undergone the A/D conversion.

Then, in step SE3, the bottom dead center signal processing unit 103 obtains the average value of the extracted pieces of data, and in step SE4, the bottom dead center signal processing unit 103 obtains a bottom dead center value by performing averaging processing on the average value with respect to a predetermined number of shots. Subsequently, this process is ended (END).

Upon the process shown in FIG. 13 being started, in step SF1, the score calculation unit 106 calculates the abnormality prediction score, using the elastic wave power value calculated by the elastic wave signal processing unit 105 and the bottom dead center value calculated by the bottom dead center signal processing unit 103. Specifically, the score calculation unit 106 obtains a corrected elastic wave power value by multiplying the elastic wave power value by an elastic wave coefficient, and obtains a corrected bottom dead center value by multiplying the bottom dead center value by the bottom dead center coefficient. Then, the score calculation unit 106 calculates the sum of the corrected elastic wave power value and the corrected bottom dead center value as the abnormality prediction score.

In the subsequent step SF2, the abnormality prediction unit 57 displays the score value of the abnormality prediction score obtained in step SF1, and notifies the operator of the timing of preparing for the replacement of the die 10, or the timing of replacing the die 10, for example, according to the score value. Subsequently, this process is ended (END).

The above-described steps SD1 to SD6 correspond to the elastic wave component obtaining step in which elastic waves generated in processing portion of the die 10 during the stamping performed by the press machine 1 using the die 10 are detected by the AE sensor 62, and values regarding the elastic waves (the elastic wave power values) are obtained based on the output signal from the AE sensor 62.

The above-described steps SE1 to SE4 correspond to the die state component obtaining step in which a parameter (a bottom dead center) other than parameters regarding elastic waves, out of the parameters regarding the state of the die 10 during the stamping performed by the press machine 1 using the die 10, is detected by the bottom dead center detection sensor 111, and a value regarding the state of the die 10 (a bottom dead center value) is obtained based on the output signal from the bottom dead center detection sensor 111.

The above-described step SF1 corresponds to the score calculation step in which the abnormality prediction score of the die 10 is calculated based on the values obtained in the elastic wave component obtaining step and the die state component obtaining step. The above-described step SF2 corresponds to the abnormality prediction step in which the occurrence of an abnormality in the die 10 is predicted based on the result of the calculation in the score calculation step.

Note that the score calculation unit 106 may simultaneously perform process to values obtained in FIGS. 11 and 12, or perform process either one of the values first.

As described above, according to the present embodiment, during the stamping performed by the press machine 1 using the die 10, the die abnormality prediction system 100 detects elastic waves generated in the processing portion of the die 10, using the AE sensor 62, and detects the bottom dead center of the stripper plate 15 during the stamping, using the bottom dead center detection sensor 111. Then, the die abnormality prediction system 100 calculates the abnormality prediction score based on the elastic wave signal detected by the AE sensor 62 and the bottom dead center signal detected by the bottom dead center detection sensor 111, and predicts an abnormality occurring in the die 10, using the abnormality prediction score.

Therefore, with the configuration of the die abnormality prediction system 100 according to the present embodiment as well, it is possible to accurately detect the degree of abrasion to the die 10. Therefore, it is possible to obtain the die abnormality prediction system 100 that is capable of accurately predicting an abnormality occurring in the die 10.

The die abnormality prediction system 100 obtains the abnormality prediction score by calculating the sum of the corrected elastic wave power value and the corrected bottom dead center value, which have been obtained by assigning a weight to the elastic wave power value of a predetermined frequency band, obtained from the elastic wave signal, and to the bottom dead center value obtained from the bottom dead center signal, by multiplying them by their respective predetermined coefficients. Thus, it is possible to accurately obtain the abnormality prediction score by using the values detected by the AE sensor 62 and the bottom dead center detection sensor 111. Therefore, it is possible to accurately estimate the current degree of abrasion to the die 10, and it is possible to accurately predict an abnormality occurring in the die 10.

Note that in the present embodiment, the position of the bottom dead center of the stripper plate 15 is used as the position of the die 10. However, this is not essential, and it is also possible to use another position of the die 10 as long as the stamping state can be detected at the position.

Other Embodiments

Although embodiments of the present invention have been described above, the embodiments are merely examples for carrying out the present invention. The present invention is not limited to the above-described embodiments, and it is possible to carry out the invention by modifying the above-described embodiments without departing from the sprit thereof.

In the above-described embodiments, the die abnormality prediction systems 50 and 100 predicts an abnormality occurring in the die 10 by using the output signals from the AE sensor 62 and the stamping load detection sensor 61 or the output signals from the AE sensor 62 and the bottom dead center detection sensor 111.

However, the die abnormality prediction systems may predict an abnormality occurring in the die 10 by using the output signals from the AE sensor 62, the stamping load detection sensor 61, and the bottom dead center detection sensor 111. In other words, it is also possible to calculate the abnormality prediction score by using the value obtained from the output signal (the elastic wave signal) from the AE sensor 62, the value obtained from the output signal (the stamping load signal) from the stamping load detection sensor 61, and the value obtained from the output signal (the bottom dead center signal) from the bottom dead center detection sensor 111, and to predict an abnormality occurring in the die 10 based on the abnormality prediction score. In this case as well, weights are assigned to the values obtained from the output signals from the sensors by multiplying the values by predetermined coefficients, and the abnormality prediction score is calculated by calculating the sum of the results of multiplication.

Sensors used together with the AE sensor 62 may be a sensor other than the stamping load detection sensor 61 or the bottom dead center detection sensor 111 insofar as the sensor can be used for estimating the state of the die (e.g. the degree of abrasion). Furthermore, it is also possible to calculate the abnormality prediction score by using the output signal from the AE sensor 62 and the output signals from a plurality of sensors (e.g. three or more sensors).

Examples of the aforementioned other sensors include a sensor that detects the position of or the distance to the upper die 11 (e.g. a rotary encoder for detecting the position of the crankshaft 36), a sensor that detects vibrations or sound during stamping (e.g. an accelerometer), a sensor that detects the temperature of the main body of the press machine 1, the temperature of the punches 14 of the die 10, or the temperature of lubricant oil for the press machine 1 (e.g. a thermocouple or a thermograph), and a sensor that detects the amount of lubricant oil flowing in the press machine 1 (e.g. a flow rate sensor). Note that the above-described other sensors correspond to the stamping state detection unit.

In the above-described embodiments, the die abnormality prediction systems 50 and 100 are applied to the press machine 1 that punches a predetermined shape out of the plate material M, using the die 10. However, the die abnormality prediction systems 50 and 100 may be applied to a press machine having a different configuration, such as a press machine that performs bending, raising, etc., in addition to the press machine that performs stamping and shearing on a material. The method for driving the press machine is not limited to the crown press method adopted in the embodiments, and may be another driving method such as a link press method, a servo press method, or a hydraulic press method.

What is claimed is:

1. A die abnormality prediction system for predicting an abnormality in a die that is used in a press machine, comprising:

an acoustic emission (AE) sensor configured to detect an elastic wave that occurs in a processing portion of the die during stamping performed by the press machine using the die;

a stamping state detection unit configured to detect a parameter other than a parameter regarding the elastic wave, out of parameters regarding a state of the die during the stamping performed by the press machine using the die;

a score calculation unit configured to calculate an abnormality prediction score of the die based on an output signal from the AE sensor and an output signal from the stamping state detection unit; and an abnormality prediction unit configured to predict an abnormality occurring in the die, based on a result of the calculation performed by the score calculation unit.

2. The die abnormality prediction system according to claim 1, wherein the score calculation unit is configured to calculate weighted values by assigning a weight to a value calculated based on the output signal from the AE sensor, and to a value calculated based on the output signal from the stamping state detection unit, and to obtain a sum of the weighted values as the abnormality prediction score.

3. The die abnormality prediction system according to claim 1, wherein the die is a die that is used for shearing.

4. The die abnormality prediction system according to claim 1, wherein the stamping state detection unit is a force sensor configured to detect a stamping load during the stamping performed by the press machine using the die.

5. The die abnormality prediction system according to claim 4, wherein the score calculation unit is configured to calculate weighted values by assigning a weight to an area value obtained by calculating an area of power values in each frequency band, using a result of power spectrum calculation based on the output signal from the AE sensor, and to a maximum amplitude of the stamping load obtained based on the output signal from the stamping state detection unit, and to obtain a sum of the weighted values as the abnormality prediction score.

6. The die abnormality prediction system according to claim 1, wherein the stamping state detection unit is a die position detection sensor configured to detect a position of the die during the stamping performed by the press machine using the die, in terms of a direction in which the stamping is performed.

7. The die abnormality prediction system according to claim 6, wherein the score calculation unit is configured to calculate weighted values by assigning a weight to a power value of a predetermined frequency band obtained by performing a power spectrum calculation based on the output signal from the AE sensor, and to position data obtained based on the output signal from the die position detection sensor, and to obtain a sum of the weighted values as the abnormality prediction score.

8. A press machine provided with the die abnormality prediction system according to claim 1.

9. A die abnormality prediction method for predicting an abnormality in a die that is used in a press machine, comprising:

an elastic wave component obtaining step of detecting, using an acoustic emission (AE) sensor, an elastic wave that occurs in a processing portion of the die during stamping performed by the press machine using the die, and obtaining a value regarding the elastic wave based on an output signal from the AE sensor;

a die state component obtaining step of detecting, using a stamping state detection unit, a parameter other than a parameter regarding the elastic wave, out of parameters regarding a state of the die during the stamping performed by the press machine using the die, and obtaining a value regarding the state of the die based on the output signal from the stamping state detection unit;

a score calculation step of calculating an abnormality prediction score of the die based on the value obtained in the elastic wave component obtaining step and the value obtained in the die state component obtaining step; and an abnormality prediction step of predicting an abnormality occurring in the die, based on a result of the calculation performed in the score calculation step.

10. The die abnormality prediction method according to claim 9, wherein in the score calculation step, weighted values are calculated by assigning a weight to a value obtained in the elastic wave component obtaining step and to a value obtained in the die state component obtaining step, and a sum of the weighted values is obtained as the abnormality prediction score.

11. The die abnormality prediction method according to claim 9, wherein the die is a die that is used for shearing.

12. The die abnormality prediction method according to claim 9, wherein the stamping state detection unit is a force sensor that is configured to detect a stamping load during the stamping performed by the press machine using the die.

13. The die abnormality prediction method according to claim 12, wherein in the score calculation step, a power area value is obtained by calculating an area of power values in each frequency band, using a result of power spectrum calculation based on the output signal from the AE sensor, a maximum amplitude of the stamping load is obtained based on the output signal from the stamping state detection unit, and weighted values are obtained by assigning a weight to the power area value and to the maximum amplitude, and a sum of the weighted values is obtained as the abnormality prediction score.

14. The die abnormality prediction method according to claim 9, wherein the stamping state detection unit is a die position detection sensor configured to detect a position of the die during the stamping performed by the press machine using the die.

15. The die abnormality prediction method according to claim 14, wherein in the score calculation step, weighted values are calculated by assigning a weight to a power value of a predetermined frequency band obtained by performing a power spectrum calculation based on the output signal from the AE sensor, and to position data obtained based on the output signal from the die position detection sensor, and a sum of the weighted values is obtained as the abnormality prediction score.

* * * * *